US008709463B2

(12) United States Patent
Looney et al.

(10) Patent No.: US 8,709,463 B2
(45) Date of Patent: Apr. 29, 2014

(54) HEMOSTATIC DEVICES AND METHODS OF MAKING SAME

(75) Inventors: Dwayne Lee Looney, Flemington, NJ (US); Kenneth Troger, Plainsboro, NJ (US); Bruce Lamb, Richboro, PA (US); Benjamin Walthall, Whitehouse Station, NJ (US)

(73) Assignee: Ethicon, Inc., Somerville, NJ (US)

( * ) Notice: Subject to any disclaimer, the term of this patent is extended or adjusted under 35 U.S.C. 154(b) by 870 days.

(21) Appl. No.: 11/454,805

(22) Filed: Jun. 16, 2006

(65) Prior Publication Data

US 2006/0233869 A1 Oct. 19, 2006

Related U.S. Application Data

(62) Division of application No. 10/603,320, filed on Jun. 25, 2003, now abandoned.

(51) Int. Cl.
*A61F 2/00* (2006.01)

(52) U.S. Cl.
USPC .......................................... 424/423

(58) Field of Classification Search
USPC .......................................... 424/423
See application file for complete search history.

(56) References Cited

U.S. PATENT DOCUMENTS

| | | | |
|---|---|---|---|
| 2,517,772 | A | 8/1950 | Doub et al. |
| 2,773,000 | A | 12/1956 | Masci et al. |
| 2,914,444 | A | 11/1959 | Smith |
| 3,328,259 | A | 6/1967 | Anderson |
| 3,328,529 | A | 6/1967 | Anderson |
| 3,364,200 | A | 1/1968 | Ashton et al. |
| 3,868,955 | A | 3/1975 | Siragusa et al. |
| 4,289,824 | A | 9/1981 | Smith |
| 4,407,787 | A | 10/1983 | Stemberger |
| 4,600,574 | A | 7/1986 | Lindner |
| 4,626,253 | A | 12/1986 | Broadnax, Jr. |
| 4,752,466 | A | 6/1988 | Saferstein et al. |
| 4,840,626 | A | 6/1989 | Linksy |
| 5,134,229 | A | 7/1992 | Saferstein et al. |
| 5,180,398 | A | 1/1993 | Boardman et al. |
| 5,409,703 | A | 4/1995 | Hall et al. |
| 5,643,596 | A | 7/1997 | Pruss et al. |
| 5,645,849 | A | 7/1997 | Pruss et al. |
| 5,821,343 | A | 10/1998 | Keogh |
| 5,866,165 | A | 2/1999 | Liu et al. |
| 5,914,118 | A | 6/1999 | Yamamura et al. |
| 5,925,552 | A | 7/1999 | Keogh et al. |
| 5,945,319 | A | 8/1999 | Keogh |
| 6,017,741 | A | 1/2000 | Keogh |
| 6,214,808 | B1 | 4/2001 | Soe et al. |
| 6,261,679 | B1 | 7/2001 | Chen et al. |
| 6,306,424 | B1 | 10/2001 | Vyakarnam et al. |
| 6,333,029 | B1 | 12/2001 | Vyakarnam et al. |
| 6,365,149 | B2 | 4/2002 | Vyakarnam et al. |
| 6,500,777 | B1 | 12/2002 | Wiseman et al. |
| 2001/0025154 | A1 | 9/2001 | Rapp |
| 2002/0012693 | A1 | 1/2002 | Diegelmann et al. |
| 2002/0120348 | A1 | 8/2002 | Melican et al. |
| 2003/0073663 | A1 | 4/2003 | Wiseman et al. |
| 2004/0005350 | A1 | 1/2004 | Looney et al. |

FOREIGN PATENT DOCUMENTS

| | | |
|---|---|---|
| CN | 1181980 | 5/1998 |
| EP | 0177064 A | 4/1986 |
| EP | 0216378 | 4/1987 |
| EP | 0372696 A | 6/1990 |
| EP | 0372969 | 6/1990 |
| EP | 0468114 A2 | 1/1992 |
| EP | 0636378 A | 2/1995 |
| EP | 1172115 A1 | 1/2002 |
| EP | 1378255 | 1/2007 |
| EP | 0815879 | 1/2008 |
| GB | 0942305 A | 11/1963 |
| GB | 0983073 A | 2/1965 |
| GB | 2314840 | 1/1998 |
| GB | 2314842 A | 1/1998 |
| GB | 2344519 A | 6/2000 |
| GB | 2399289 A | 9/2004 |
| IN | 159332 | 5/1987 |
| JP | 60087225 A | 5/1985 |
| JP | 63-57046 | 3/1988 |
| JP | 9-51912 | 2/1997 |
| JP | 11-511354 | 10/1999 |
| JP | 2001-340375 | 12/2001 |
| JP | 2002-52077 | 2/2002 |
| RU | 2235539 | 9/2004 |
| WO | WO 96/16643 A | 6/1996 |
| WO | WO 96/40033 A1 | 12/1996 |
| WO | WO 98/00180 A1 | 1/1998 |
| WO | WO 98/00446 A | 1/1998 |
| WO | WO 98/33479 A | 8/1998 |
| WO | WO 99/01166 A1 | 1/1999 |

(Continued)

OTHER PUBLICATIONS

Jackson, E. L. et al., J. Am. Chem. Soc, (1937), 59, 2049-2050.
Davidson, G. F., The Journal of the Textile Institute Transactions (1940), 81-96.
Frantz, V. K. et al., J. Am. Med. Assoc., (1945), 129, 798-801.
Frantz, V. K., The Bulletin, (1946), 22, 102-110.
Lucas, O. N., Journal of Oral Therapeutics and Pharmacology, vol. 3, No. 4, (1967), 262-268.
Singh, M., Journal of Biomedical Materials Research, vol. 15, (1981), 655-661.
Matras, H., J. Oral Maxillofac Surg, vol. 43, (8), (1985), 605-611.
Sinha, T. J. M. et al. Biomater., Med. Devices, Artif. Organs (1985), 12(3-4), 273-87.

(Continued)

Primary Examiner — Jake Vu
(74) Attorney, Agent, or Firm — David R. Crichton; Leo B. Kriksunov

(57) ABSTRACT

The present invention includes compositions suitable for use in a hemostatic device and hemostatic devices utilizing such compositions, as well as methods of making the compositions and the medical devices utilizing such compositions where the compositions contain biocompatible, oxidized cellulose particles having an average designated nominal particle size of about 0.035-4.35 mm and a biocompatible, water-soluble or water-swellable polysaccharide porous binder component.

3 Claims, 22 Drawing Sheets

(56) References Cited

FOREIGN PATENT DOCUMENTS

| WO | WO 01/22059 A2 | 3/2001 |
|---|---|---|
| WO | WO 01/23653 A1 | 4/2001 |
| WO | WO 02/02155 A1 | 1/2002 |
| WO | WO 02/22059 A1 | 3/2002 |
| WO | WO 02/058750 A2 | 8/2002 |
| WO | WO 03/020191 A | 3/2003 |

OTHER PUBLICATIONS

Arand, A. G. et. al. Neurosurgery vol. 18, No. 2, (1986), 223-233.
Turaev, A. S. et al. Khim.-Farm. Zh. (1990), 24(8), 47-51.
Stilwell, R. L. et al. Handbook of Biodegradable Polymers (1997), 291-306.
Edwards, J. V. et al. Wound Rep. and Reg., vol. 9, No. 1, (2001), 50-58.
Hercules Aqualon® Sodium Carboxmethylcellulose Product Specifications No. 4116-4, 1997.
Hercules Aqualon® Sodium Carboxmethylcellulose Physical and Chemical Properties, 1995.
European Search Report dated Dec. 17, 2003 for corresponding EP03254114.
European Search Report dated Apr. 2, 2004 for corresponding EP03254119.5.
European Search Report dated Jul. 15, 2004 for corresponding EP03254091.6.
European Search Report dated Oct. 25, 2004 for corresponding EP04253808.2.
U.S. Appl. No. 10/186,021, J.X. Guo et al.
U.S. Appl. No. 10/304,472, S.M. Pendharkar et al.
U.S. Appl. No. 10/304,781, S.M. Pendharkar.
U.S. Appl. No. 10/305,040, S.M. Pendharkar.
U.S. Appl. No. 10/326,244, G. Zhang et al.
U.S. Appl. No. 10/396,224, D.L. Looney et al.
U.S. Appl. No. 10/396,226, D.L. Looney et al.
U.S. Appl. No. 10/448,878, S.M. Pendharkar et al.
U.S. Appl. No. 10/603,320, D.L. Looney.
U.S. Appl. No. 10/721,836, D.L. Looney et al.

HEMOSTATIC DEVICES AND METHODS OF MAKING SAME

CROSS-REFERENCE TO RELATED APPLICATIONS

This application is a divisional of U.S. application Ser. No. 10/603,320, filed Jun. 25, 2003 now abandoned.

FIELD OF THE INVENTION

The present invention relates to compositions suitable for use in hemostatic devices, hemostatic devices utilizing such compositions and methods of making such compositions and hemostatic devices.

BACKGROUND OF THE INVENTION

The control of bleeding is essential and critical in surgical procedures to minimize blood loss, to reduce post-surgical complications, and to shorten the duration of the surgery in the operating room. Due to its biodegradability and its bactericidal and hemostatic properties, cellulose that has been oxidized to contain carboxylic acid moieties, hereinafter referred to as carboxylic-oxidized cellulose, has long been used as a topical hemostatic wound dressing in a variety of surgical procedures, including neurosurgery, abdominal surgery, cardiovascular surgery, thoracic surgery, head and neck surgery, pelvic surgery and skin and subcutaneous tissue procedures.

Currently utilized hemostatic wound dressings include knitted or non-woven fabrics comprising carboxylic-oxidized cellulose. Currently utilized oxidized cellulose is carboxylic-oxidized regenerated cellulose comprising reactive carboxylic acid groups and which has been treated to increase homogeneity of the cellulose fiber. Examples of such hemostatic wound dressings commercially available include Surgicel® absorbable hemostat; Surgicel Nu-Knit® absorbable hemostat; and Surgicel® Fibrillar absorbable hemostat; all available from Johnson & Johnson Wound Management Worldwide, a division of Ethicon, Inc., Somerville, N.J., a Johnson & Johnson Company. Other examples of commercial absorbable hemostats containing carboxylic-oxidized cellulose include Oxycel® absorbable cellulose surgical dressing from Becton Dickinson and Company, Morris Plains, N.J., and Curacel® oxidized regenerated cellulose powder from Curaspon Healthcare, the Netherlands.

Hemostatic devices utilizing carboxylic-oxidized cellulose, due to its acidic pH, are known to rapidly denature acid-sensitive, hemostatic proteins, including thrombin or fibrinogen, on contact. Thus, it is problematic to use the carboxylic-oxidized cellulose as a carrier for acid-sensitive species, such as thrombin and fibrinogen, as well as other acid-sensitive biologics and pharmaceutical agents.

In addition to issues concerning compatibility of conventional carboxylic-oxidized cellulose with "acid-sensitive" species, e.g. proteins, drugs, etc., while the absorbency of body fluid and the hemostatic action of such currently available carboxylic-oxidized cellulose hemostats are adequate for applications where mild to moderate bleeding is encountered, they are not known to be effective to provide and maintain hemostasis in cases of severe bleeding where a relatively high volume of blood is lost at a relatively high rate. In such instances, e.g. arterial puncture, liver resection, blunt liver trauma, blunt spleen trauma, aortic aneurysm, bleeding from patients with over-anticoagulation, or patients with coagulopathies, such as hemophilia, etc., a higher degree of hemostasis is required quickly.

The present invention provides devices that provide hemostatic and anti-microbial properties equivalent to or better than conventional hemostatic devices or that also may be compatible with "acid-sensitive" species, and methods for preparing such devices.

SUMMARY OF THE INVENTION

The present invention is directed to compositions suitable for use in a hemostatic device and hemostatic devices utilizing such compositions, where the compositions comprise biocompatible, oxidized cellulose particles having an average designated nominal particle size of about 0.035-4.35 mm; and a biocompatible, water-soluble or water-swellable polysaccharide porous binder component. The invention also is directed to methods of making the compositions and the medical devices utilizing such compositions.

BRIEF DESCRIPTION OF THE FIGURES

FIG. 7 is a scanning electron microscopy image (×50) of a cross section of a wound dressing described in Example 1a.

FIG. 8a is a scanning electron microscopy image (×50) of the first surface of a wound dressing described in example 1a.

FIG. 8b is a scanning electron microscopy image (×250) of the first surface of a wound dressing described in example 1a.

FIG. 9a is a scanning electron microscopy image (×50) of the second opposing surface of a wound dressing described in example 1a.

FIG. 9b is a scanning electron microscopy image (×250) of the second opposing surface of a wound dressing described in example 1a.

DETAILED DESCRIPTION OF THE INVENTION

Figure 1:
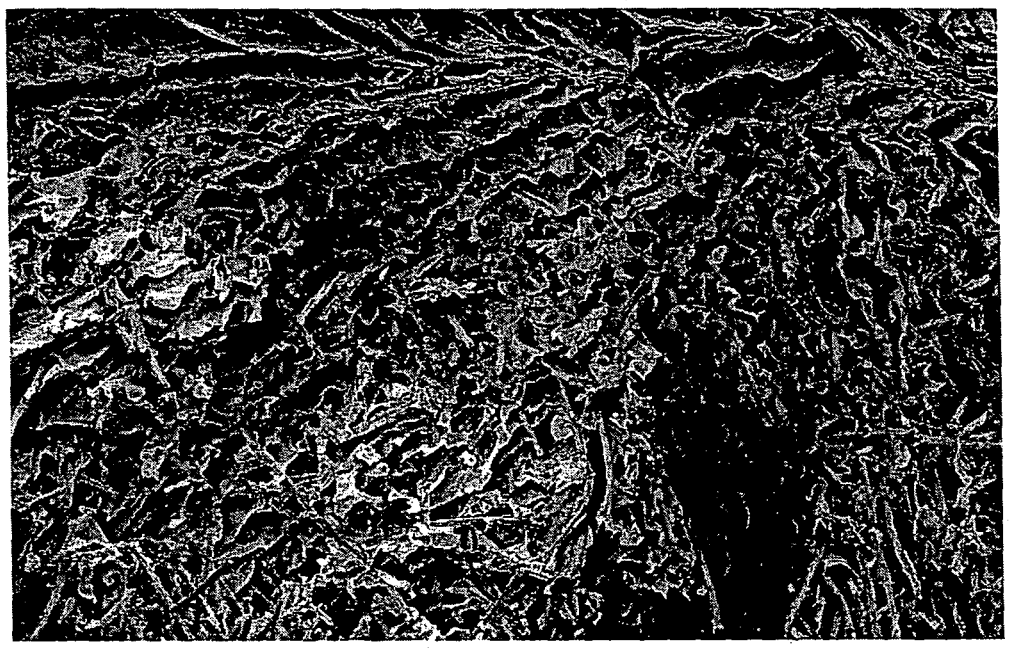
FIG. 1 is a scanning electron microscopy image (×50) of a cross section of a wound dressing described in example 1c
Figure 2A:
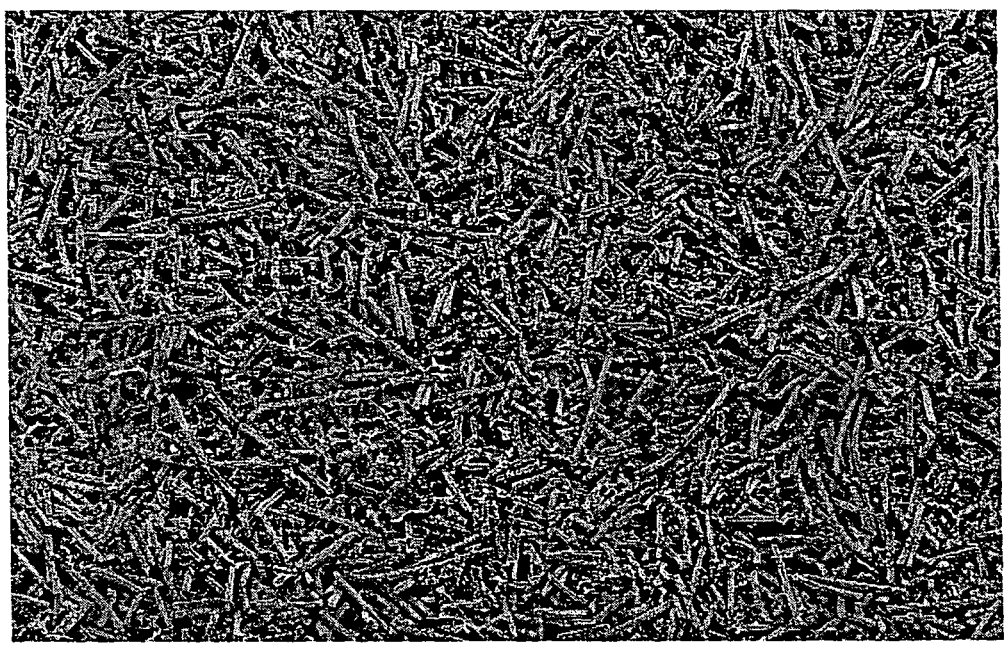
FIG. 2a is a scanning electron microscopy image (×50) of the first surface of a wound dressing described in example 1c.
Figure 2B:
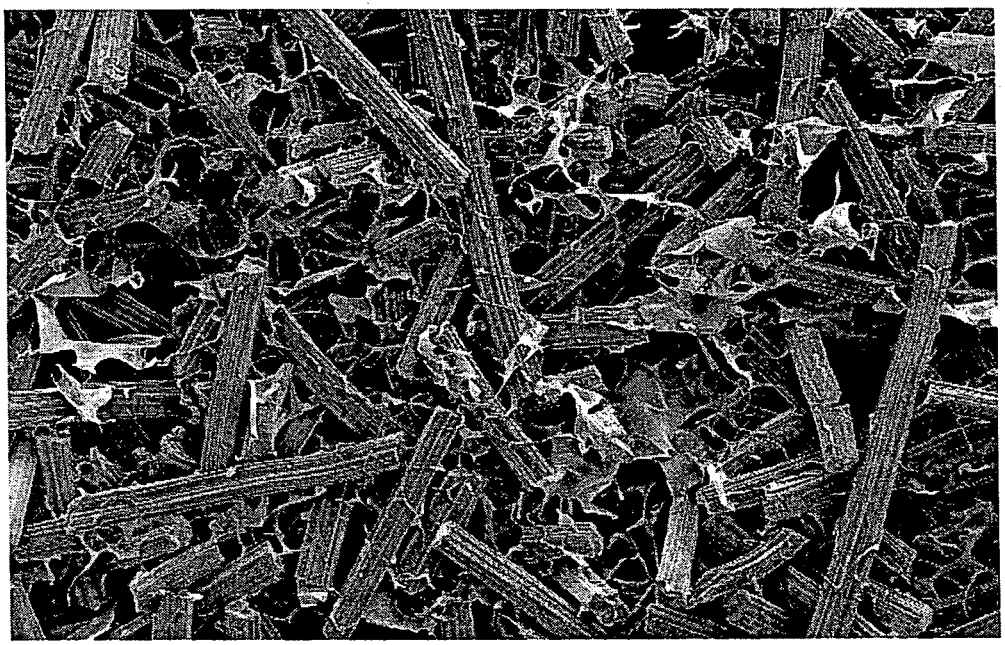
FIG. 2b is a scanning electron microscopy image (×250) of the first surface of a wound dressing-described in example 1c.
Figure 3A:
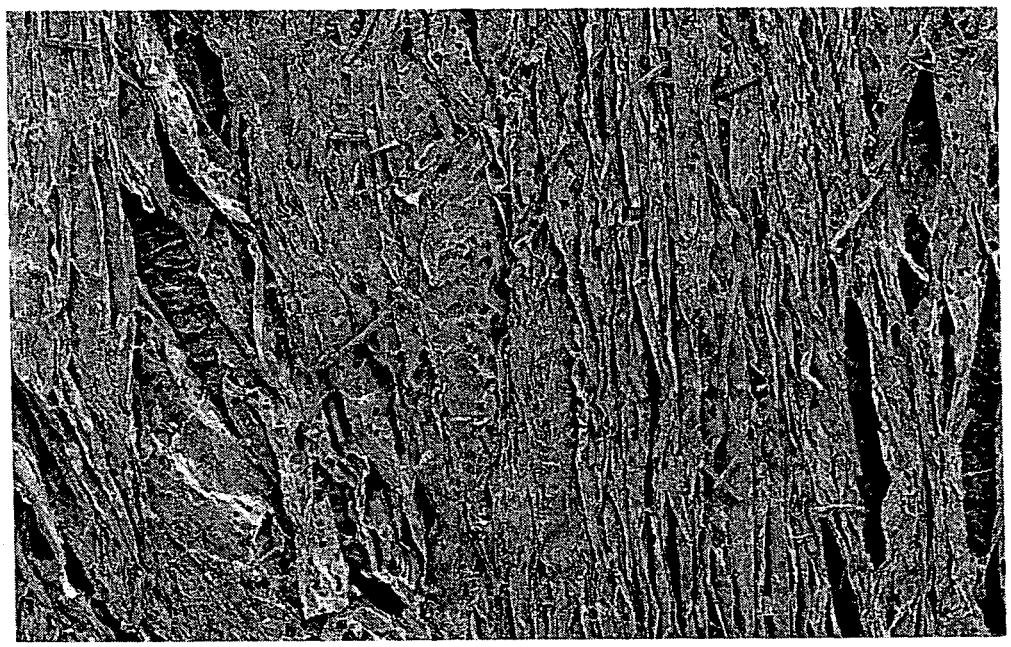
FIG. 3a is a scanning electron microscopy image (×50) of the second opposing surface of a wound dressing described in example 1c.
Figure 3B:
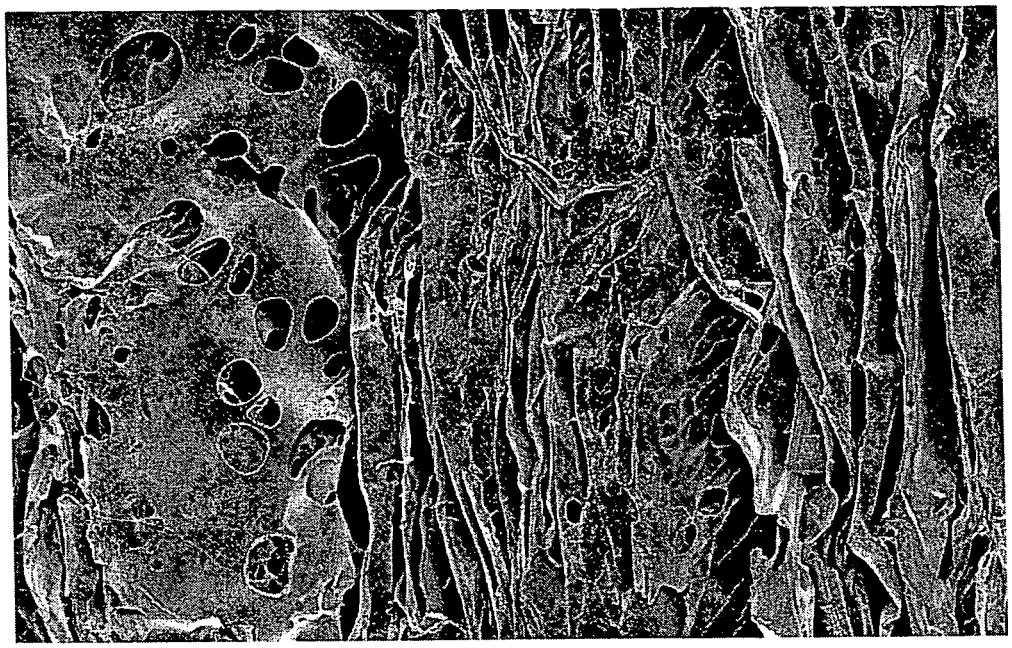
FIG. 3b is a scanning electron microscopy image (×250) of the second opposing surface of a wound dressing described in example 1c.
Figure 4:
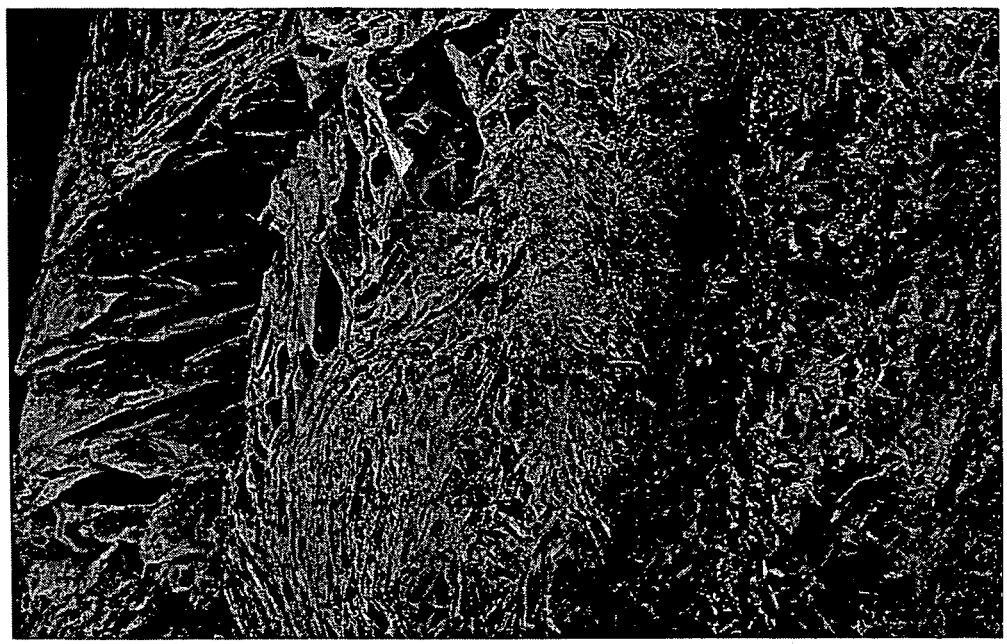
FIG. 4 is a scanning electron microscopy image (×50) of a cross section of a wound dressing described in example 1b
Figure 5A:
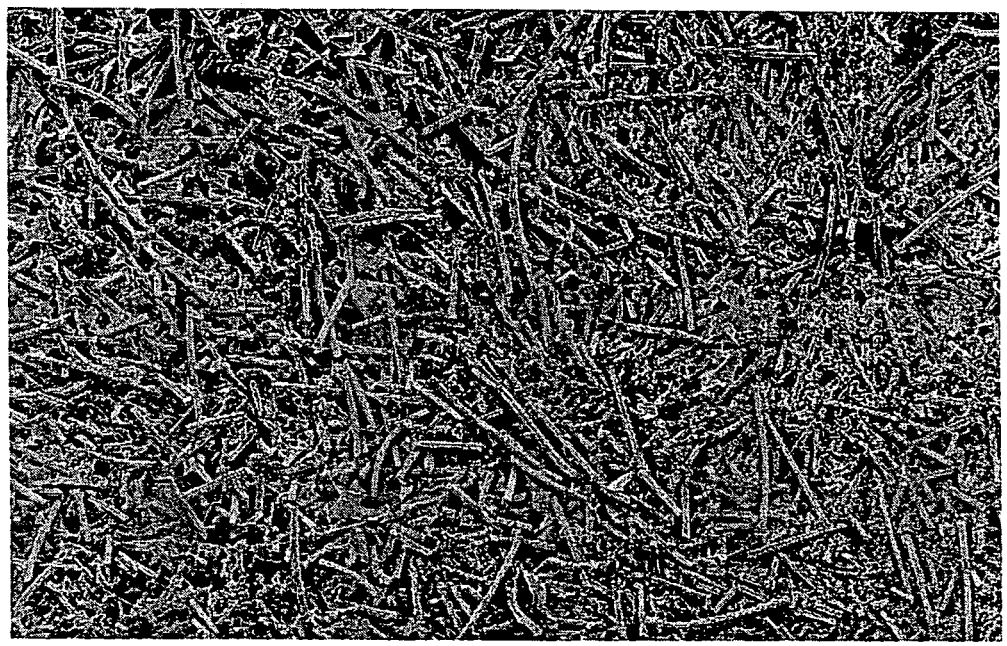
FIG. 5a is a scanning electron microscopy image (×50) of the first surface of a wound dressing described in example 1b.
Figure 5B:
FIG. 5b is a scanning electron microscopy image (×250) of the first surface of a wound dressing described in example 1b.
Figure 6A:
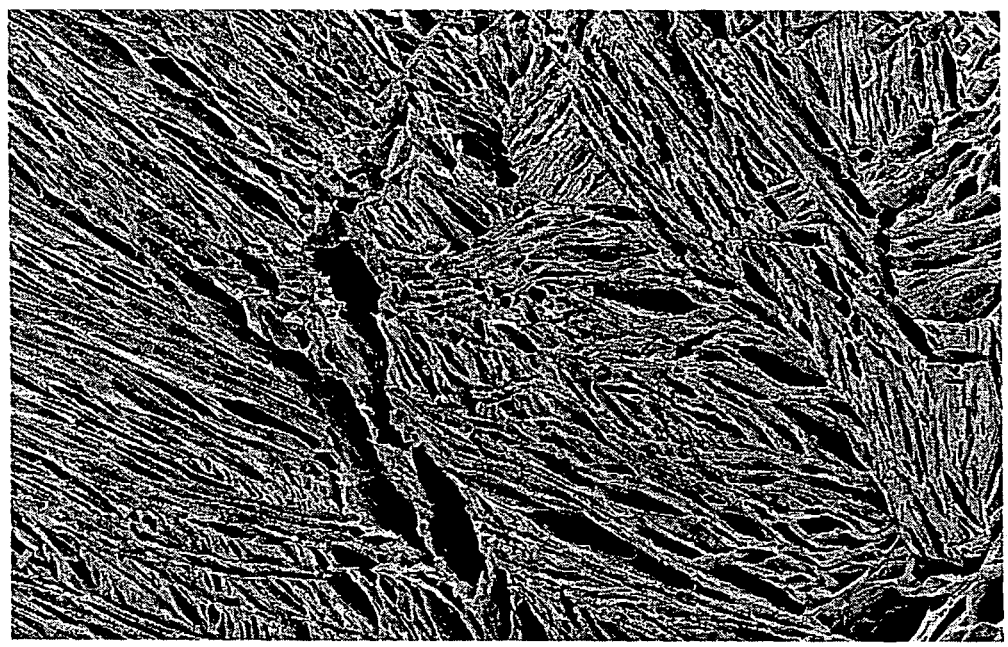
FIG. 6a is a scanning electron microscopy image (×50) of the second opposing surface of a wound dressing described in example 1b.
Figure 6B:
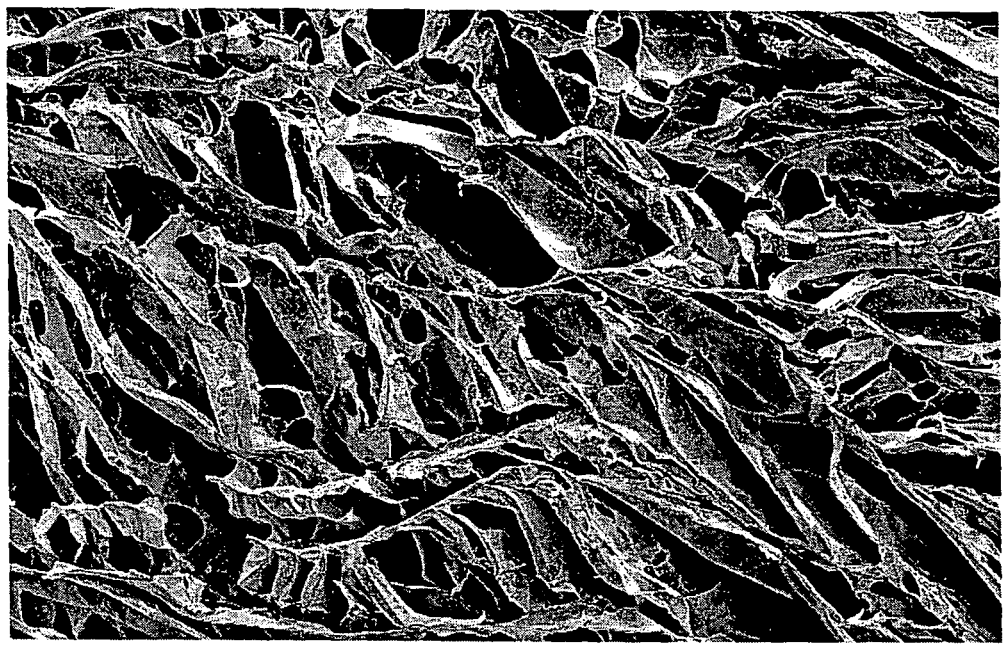
FIG. 6b is a scanning electron microscopy image (×250) of the second opposing surface of a wound dressing described in example 1b.
Figure 7:
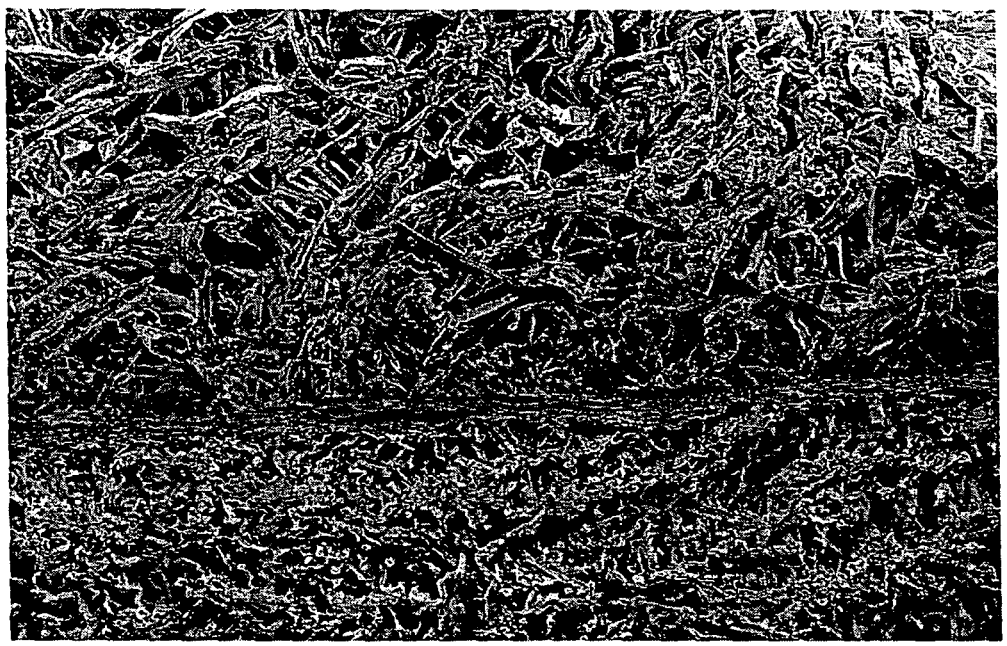
Figure 8A:
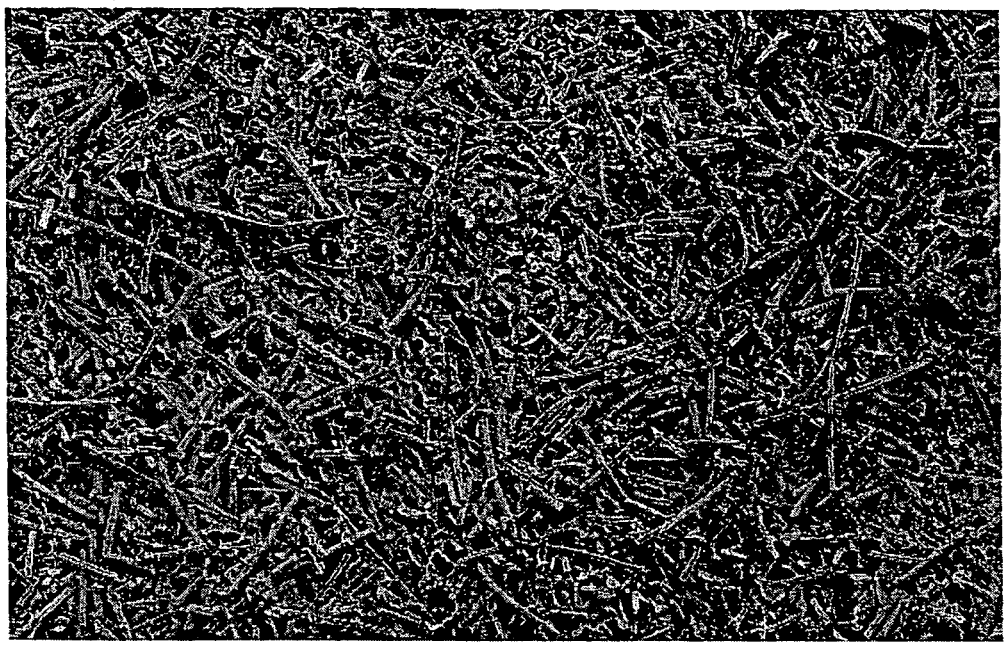
Figure 8B:
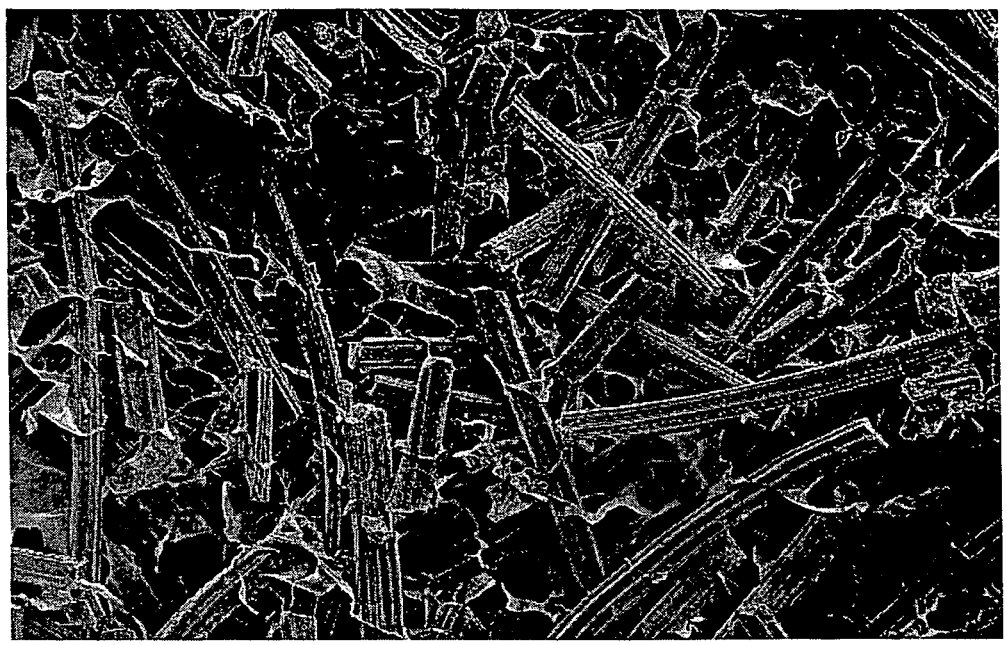
Figure 9A:
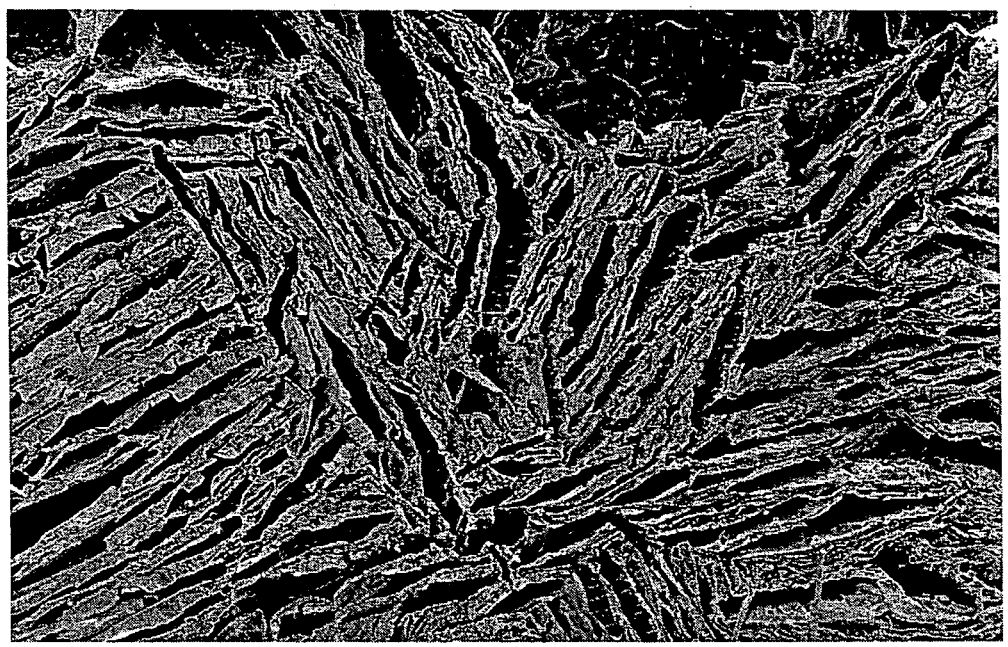
Figure 9B:
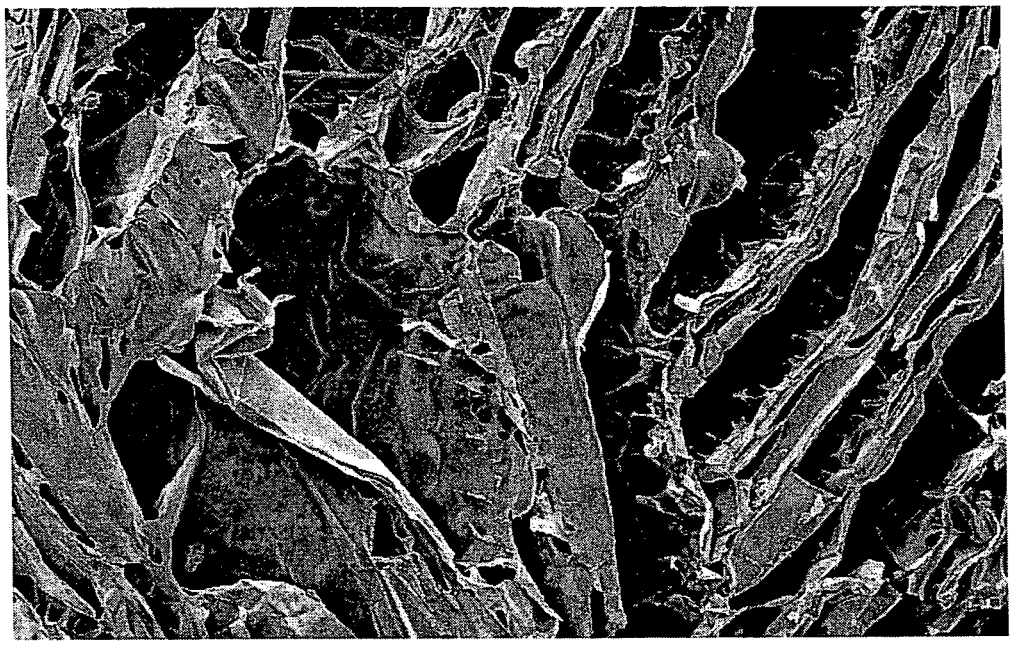
Figure 10A:
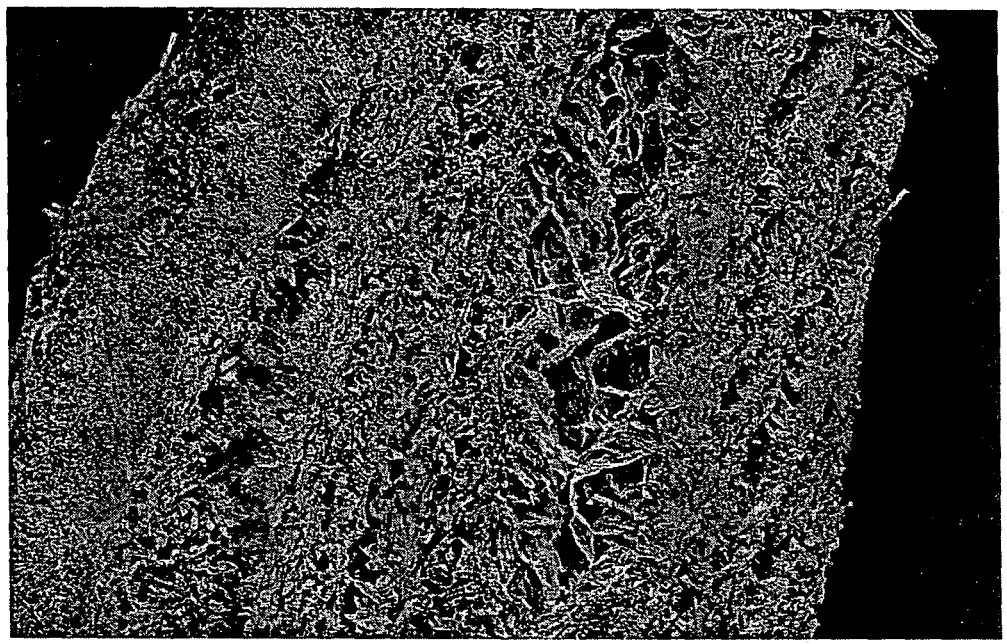
FIG. 10a is a scanning electron microscopy image (×50) of a cross section of a hemostatic device described in example 3.
Figure 10B:
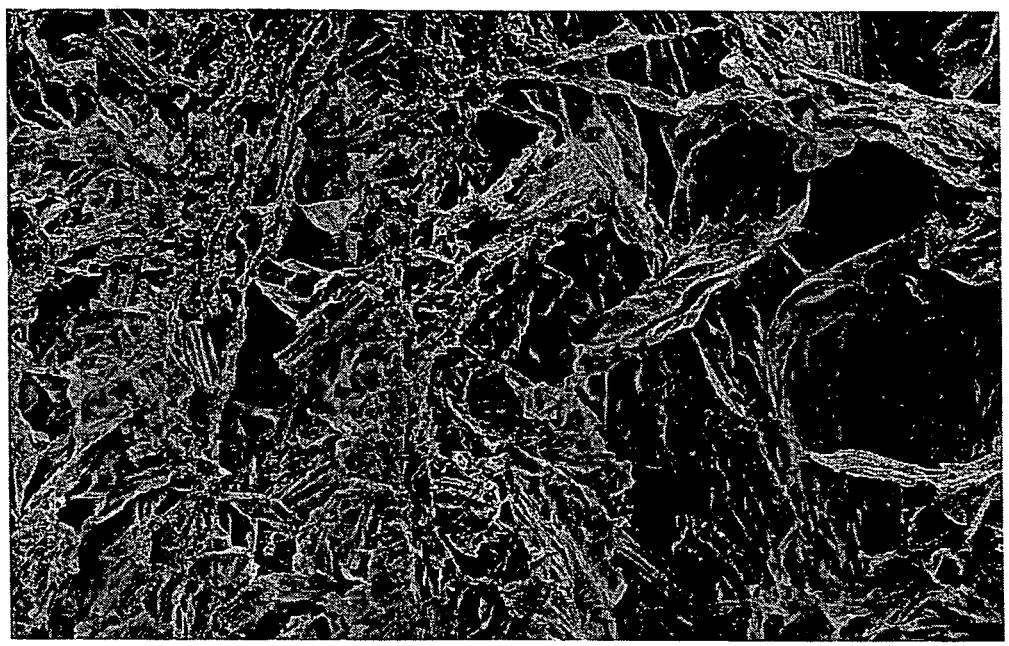
FIG. 10b is a scanning electron microscopy image (×250) of a cross section of a hemostatic device described in example 3.
Figure 11A:
FIG. 11a is a scanning electron microscopy image (×50) of a surface morphology of a hemostatic device described in example 3.
Figure 11B:
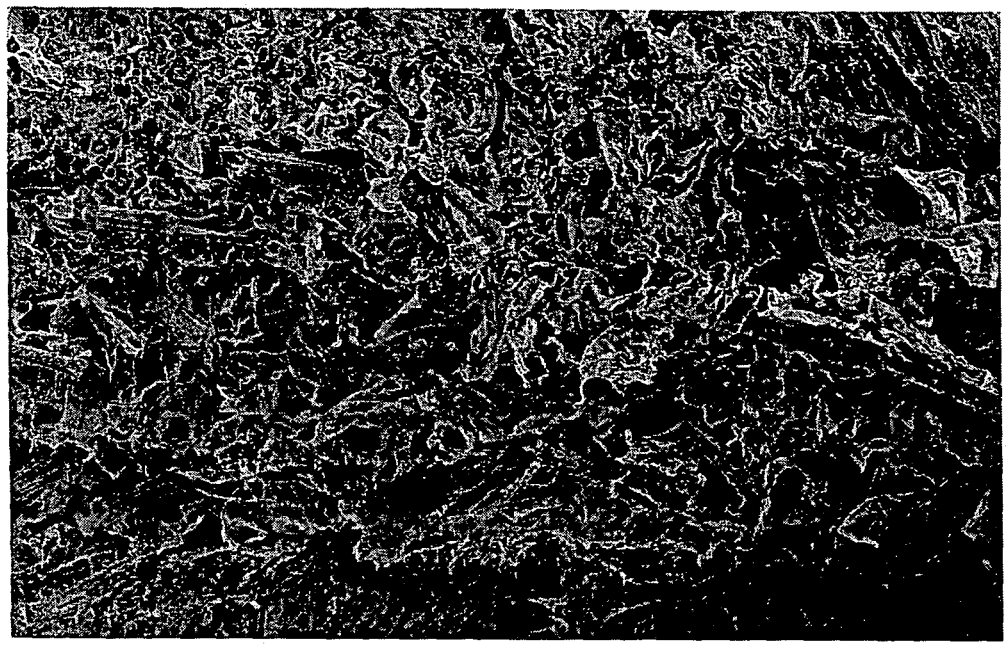
FIG. 11b is a scanning electron microscopy image (×250) of a surface morphology of a hemostatic device described in example 3.

We have discovered certain compositions that utilize biocompatible oxidized cellulose particles and a biocompatible, porous polysaccharide binder component and that possess properties suitable for use in hemostatic devices. Particles, as used herein, is meant to include various forms of solid particulate material that may be combined with a polymeric binder component to form a composition having structure, and specifically includes forms such as fibers and powders of both regular and irregular shape. The compositions comprise a porous, polymer binder component, whereby the oxidized cellulose particles are bound by the binder component so as to provide the composition with physical and chemical properties suitable for use in hemostatic devices. The physical structure of the compositions may be in the form of a foam or an agglomerate, each as described in more detail herein below.

Hemostatic devices of the present invention utilizing such compositions provide and maintain effective hemostasis when applied to a wound requiring hemostasis. Effective hemostasis, as used herein, is the ability to control and/or abate capillary, venous, or arteriole bleeding within an effective time, as recognized by those skilled in the art of hemostasis. Further indications of effective hemostasis may be provided by governmental regulatory standards and the like.

In certain embodiments, hemostatic devices of the present invention may be effective in providing and maintaining hemostasis in cases of severe bleeding. As used herein, severe bleeding is meant to include those cases of bleeding where a relatively high volume of blood is lost at a relatively high rate. Examples of severe bleeding include, without limitation, bleeding due to arterial puncture, liver resection, blunt liver trauma, blunt spleen trauma, aortic aneurysm, bleeding from patients with over-anticoagulation, or bleeding from patients with coagulopathies, such as hemophilia. Such devices allow a patient to ambulate quicker than the current standard of care following, e.g. a diagnostic or interventional endovascular procedure.

The polymer used to prepare the porous, binder component in compositions and devices of the present invention is a biocompatible, water-soluble, or water-swellable polymer. In order to provide the composition with chemical properties suitable for use in hemostatic devices, the water-soluble or water-swellable polymer must rapidly absorb blood or other body fluids and form a tacky or sticky gel adhered to tissue when placed in contact therewith. The fluid-absorbing polymer, when in a dry or concentrated state, interacts with body fluid through a hydration process. Once applied to a bleeding site, the polymer interacts with the water component in the blood via the hydration process. The hydration force not only provides an adhesive interaction that aids in the hemostatic device adhering to the bleeding site, but it also serves as a sealant at the bleeding site to stop the blood flow and thus aid in hemostatis provided by the oxidized cellulose fibers.

Preferred polymers used as a binder component include polysaccharides. Such polysaccharides include, without limitation, cellulose, alkyl cellulose, e.g. methylcellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid polyguluronic acid, and derivatives of any of the above.

Preferably, oxidized cellulose particles are used to prepare the compositions and hemostatic devices of the present invention. The oxidized cellulose may be amorphous, crystalline or a combination thereof. The oxidized cellulose may be carboxylic-oxidized cellulose or aldehyde-oxidized cellulose, each as defined and described herein. The oxidized cellulose may be oxidized regenerated cellulose, which has a higher degree of uniformity versus cellulose that has not been regenerated. Regenerated cellulose and a detailed description of how to make oxidized regenerated cellulose is set forth in U.S. Pat. No. 3,364,200, which discloses the preparation of carboxylic-oxidized cellulose with an oxidizing agent such as dinitrogen tetroxide in a Freon medium, and U.S. Pat. No. 5,180,398, which discloses the preparation of carboxylic-oxidized cellulose with an oxidizing agent such as nitrogen dioxide in a per-fluorocarbon solvent, the contents each of which is hereby incorporated by reference as if set forth in its entirety. After oxidation by either method, the carboxylic-oxidized cellulose is thoroughly washed with a solvent such as carbon tetrachloride, followed by aqueous solution of 50 percent isopropyl alcohol (IPA), and finally with 99% IPA. As such, teachings concerning oxidized regenerated cellulose and methods of making same are well within the knowledge of one skilled in the art of hemostatic devices.

Oxidized cellulose particles may be derived from an oxidized cellulose fabric that is woven or non-woven. Exemplary fabrics are described in U.S. Pat. No. 4,626,253, the contents of which is hereby incorporated by reference herein as if set forth in its entirety. The oxidized cellulose particles may be obtained from fabrics utilized in conventional hemostatic wound dressings, such as Surgicel® absorbable hemostat; Surgicel Nu-Knit® absorbable hemostat; and Surgicel® Fibrillar absorbable hemostat; all available from Johnson & Johnson Wound Management Worldwide, a division of Ethicon, Inc., Somerville, N.J., a Johnson & Johnson Company, as well as Oxycel® absorbable cellulose surgical dressing from Becton Dickinson and Company, Morris Plains, N.J. Oxidized cellulose powder such as Curacel® oxidized regenerated cellulose powder from Curaspon Healthcare, the Netherlands, also may be used in compositions and hemostatic devices of the present invention.

Embodiments of the present invention include the use of oxidized cellulose particles that are derived from absorbable hemostatic fabrics that are warp knitted tricot fabrics constructed of bright rayon yarn which is subsequently oxidized to include carboxyl or aldehyde moieties in amounts effective to provide the fabrics with biodegradability and anti-microbial activity. The fabrics are characterized by having a single ply thickness of at least about 0.5 mm, a density of at least about 0.03 g/cm$^2$, air porosity of less than about 150 cm$^3$/sec/cm$^2$, and liquid absorption capacity of at least about 3 times the dry weight of the fabric and at least about 0.1 g water per cm$^2$ of the fabric.

The tricot fabrics from which the oxidized cellulose particles may be derived may be constructed from bright rayon yarns of from about 40 to 80 total denier. Each yarn may contain from 10 to 25 individual filaments, although each individual filament preferably is less than 5 denier to avoid extended absorption times. The high bulk and fabric density are obtained by knitting at 28 gauge or finer, preferably at 32 gauge, with a fabric quality of about 10 or 12 (40 to 48 courses per inch). A long guide bar shog movement of at least 6 needle spaces, and preferably 8 to 12 spaces, further increases fabric thickness and density.

Where the oxidized cellulose is a carboxylic-oxidized cellulose, the oxidized cellulose may be conditioned prior to use. Conditioning can be achieved by storing the oxidized cellulose at room temperature under ambient conditions for at least 6 month, or conditioning can be accelerated. Alternatively, the oxidized cellulose is exposed to conditions of about 4° C. to about 90° C., at a relative humidity of from about 5% to about 90%, for a time of from about 1 hour to 48 months; conditions of about 4° C. to about 60° C., at a relative humidity of from about 30% to about 90%, for a time of from about 72 hours to 48 months; conditions of about 18° C. to about 50° C., at a relative humidity of from about 60% to about 80%, for a time of from about 72 hours to 366 hours; or conditions of about 50° C., at a relative humidity of about 70%, for a time of about 168 hours.

As a result of the conditioning, the carboxylic-oxidized cellulose particles will comprise at least about 3 weight percent of water-soluble molecules, preferably from about 3 to about 30 weight percent, more preferably from about 8 to about 20 weight percent, even more preferably from about 9 to about 12 weight percent, and most preferably about 10 weight percent. In general, the water-soluble molecules are acid-substituted oligosaccharides containing approximately 5 or fewer saccharide rings. It has been found that the hemostatic efficacy of a wound dressing derived from such carboxylic-oxidized cellulose, including the occurrence of re-bleeding of a wound for which hemostasis initially has been achieved, is improved when the contents of the water-soluble molecules reach about 8%, preferably about 10%, based on the weight of the carboxylic-oxidized cellulose.

The oxidized cellulose particles also will comprise from about 3 to about 20 weight percent of water, preferably from about 7 to about 13 weight percent, and more preferably from about 9 to about 12 weight percent water prior to use. Similar levels of moisture and water-soluble molecules in the carboxylic-oxidized cellulose also may be achieved by other means. For example, sterilization by known techniques, such as gamma or e-beam irradiation, may provide similar content of water and/or water-soluble molecules. In addition, water-soluble molecules such as oligosacchrides could be added to the oxidized cellulose particles prior to use. Once having the benefit of this disclosure, those skilled in the art may readily ascertain other methods for providing such oxidized celluloses with moisture and/or water-soluble molecules.

In some embodiments of the invention, hemostatic agents, or other biological or therapeutic compounds, moieties or species, e.g. drugs, and pharmaceutical agents, may be used. As discussed above, such agents or compounds may be "acid-sensitive", meaning that they may be degraded or denatured by, or otherwise detrimentally affected by acidic pH, such as is provided by conventional carboxylic-oxidized hemostatic wound dressings. Hemostatic devices of the present invention that are compatible with acid-sensitive species comprise oxidized cellulose derived from a biocompatible, aldehyde-oxidized polysaccharide. In such devices, the polysaccharide preferably will contain an amount of aldehyde moieties effective to render the modified polysaccharide biodegradable, meaning that the polysaccharide is degradable by the body into components that either are resorbable by the body, or that can be passed readily by the body. More particularly, the biodegraded components do not elicit permanent chronic foreign body reaction when they are absorbed by the body, such that no permanent trace or residual of the component is retained at the implantation site.

Aldehyde-oxidized polysaccharides used in the present invention may include, without limitation, cellulose, cellulose derivatives, e.g. alkyl cellulose, for instance methyl cellulose, hydroxyalkyl cellulose, alkylhydroxyalkyl cellulose, cellulose sulfate, salts of carboxymethyl cellulose, carboxymethyl cellulose and carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, heparin, heparin sulfate, heparan, heparan sulfate, dermatan sulfate, keratin sulfate, carrageenans, chitosan, starch, amylose, amylopectin, poly-N-glucosamine, polymannuronic acid, polyglucuronic acid, polyguluronic acid and derivatives of the above, each of which has been oxidized to included anti-microbial effective amounts of aldehyde moieties.

In preferred embodiments utilizing aldehyde-oxidized polysaccharides, the polysaccharide is oxidized as described herein to assure that the aldehyde-oxidized polysaccharide is biodegradable. Such biodegradable, aldehyde-oxidized polysaccharides may be represented by Structure I below.

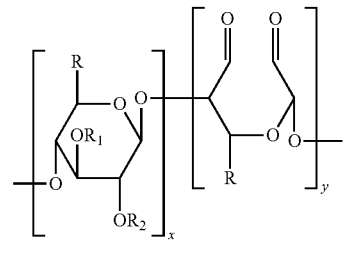

$x + y = 100\%$ where x and y represent mole percent, x plus y equals 100 percent, x is from about 95 to about 5, y is from about 5 to about 95; and R may be $CH_2OR_3$, $COOR_4$, sulphonic acid, or phosphonic acid; $R_3$ and $R_4$ may be H, alkyl, aryl, alkoxy or aryloxy, and $R_1$ and $R_2$ may be H, alkyl, aryl, alkoxy, aryloxy, sulphonyl or phosphoryl.

In certain embodiments of the present invention, the biocompatible, biodegradable hemostatic devices comprises biocompatible, biodegradable, aldehyde-oxidized regenerated cellulose. In particular, preferred aldehyde-oxidized regenerated cellulose is one comprising repeating units of Structure II:

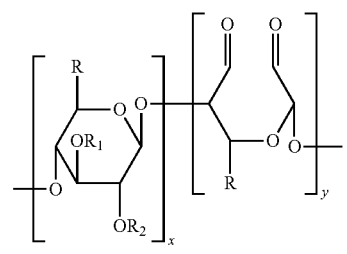

$x + y = 100\%$ where x and y represent mole percent, x plus y equals 100 percent, x is from about 95 to about 5, y is from about 5 to about 95; and R is $CH_2OH$, $R_1$ and $R_2$ are H.

In preferred embodiments of the invention, the aldehyde-oxidized regenerated polysaccharide, e.g. cellulose, is essentially free of functional or reactive moieties other than aldehyde moieties. By essentially free, it is meant that the polysaccharide does not contain such functional or reactive moieties in amounts effective to alter the properties of the aldehyde-oxidized polysaccharide, or to provide the polysaccharide with a pH of less than about 4.5, more preferably less than about 5, or greater than about 9, preferably about 9.5. Such moieties include, without limitation, carboxylic acid moieties typically present in wound dressings made from carboxyl-oxidized cellulose. Excess levels of carboxylic acid moieties will lower the pH of the dressings so that they are not compatible for use with those acid-sensitive species that may be degraded or denatured by such a low pH, e.g. thrombin. Other moieties essentially excluded include, without limitation, sulfonyl or phosphonyl moieties.

Generally, the oxidized cellulose particles of the present invention have an average designated nominal particle size of between about 0.035 mm (Tyler mesh size 400) to about 4.35 mm (Tyler mesh size 5). More preferably, the oxidized cellulose has an average designated nominal particle size of about 0.68 mm to about 4.35 mm. Most preferably, the oxidized cellulose particles have an average designated nominal particle size of from about 0.80 to about 2.20 mm (Tyler mesh size ranging from 10 to 20). By designated nominal particle size, we mean a mean distribution of a certain particle size with permissible variation range, as defined in ASTM E11-87.

Oxidized cellulose particles used in the present invention preferably have an average designated nominal particle size ranging from about 0.68 mm to about 4.35 mm. The oxidized cellulose particles used in the present invention may be made by chopping the hemostatic fabrics described above or any oxidized cellulose fabric with a cutting blade of a motor-driven mill to the desired fiber length using an Thomas-Wiley® Laboratory Mill, Intermediate Model cutting blade. The motor-driven mill, with two stationary blades and a motor with four cutting edges revolving at high speed to produce a shearing action, is ideal for rapid milling of fabric samples. For example, the oxidized cellulose particles may be made by placing an oxidized cellulose fabric, such as Surgicel® absorbable hemostat; Surgicel Nu-Knit® absorbable hemostat; or Surgicel® Fibrillar absorbable hemostat, or an oxidized cellulose, in a stainless steel foil pouch filled with liquid nitrogen and submerging the foil pouch in liquid nitrogen. The foil pouch is then passed through a dual wheel roller at, for example, 6 in/min, yielding oxidized cellulose having an average particle size of 0.035-4.35 mm.

The compositions used to make the hemostatic devices of the present invention may be made by first dissolving the water-soluble or water-swellable polymer in water to make a polymer solution. The oxidized cellulose particles, e.g. fibers, and the polymer solution may then be homogenized using an Ultra-TURRAX® T18 DIXI midi Dispersers/Homogenizers to aid the dispersion of particles throughout the solution. The homogenizer, with its mechanical action, is known for use in blending unlike materials to make a homogenous-distribution. After the oxidized cellulose particles are dispersed in the polymer solution, the dispersion is subjected to conditions under which the dissolved water-soluble or water-swellable polymer is solidified so as to provide a porous binder component for the oxidized cellulose particles. The solvent, i.e. water, then is extracted from the composition to yield a porous composition comprising the oxidized cellulose particles of desired size and the porous polymeric binder component.

Figure 12A:
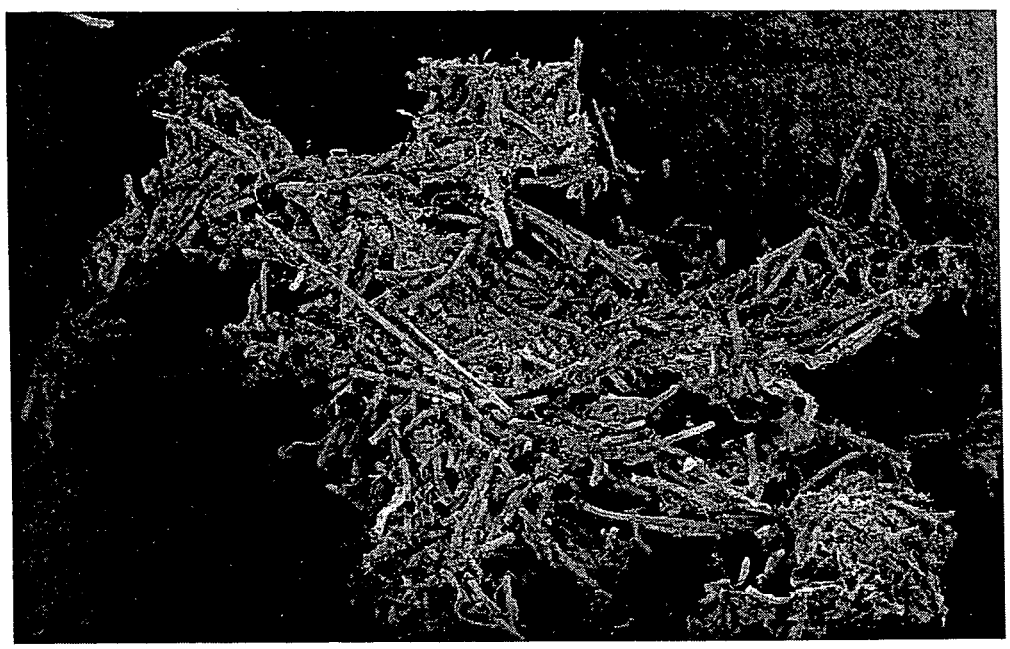
FIG. 12a is a scanning electron microscopy image (×50) of an agglomerate described in example 4.
Figure 12B:
FIG. 12b is a scanning electron microscopy image (×250) of an agglomerate described in example 4.
Figure 13:
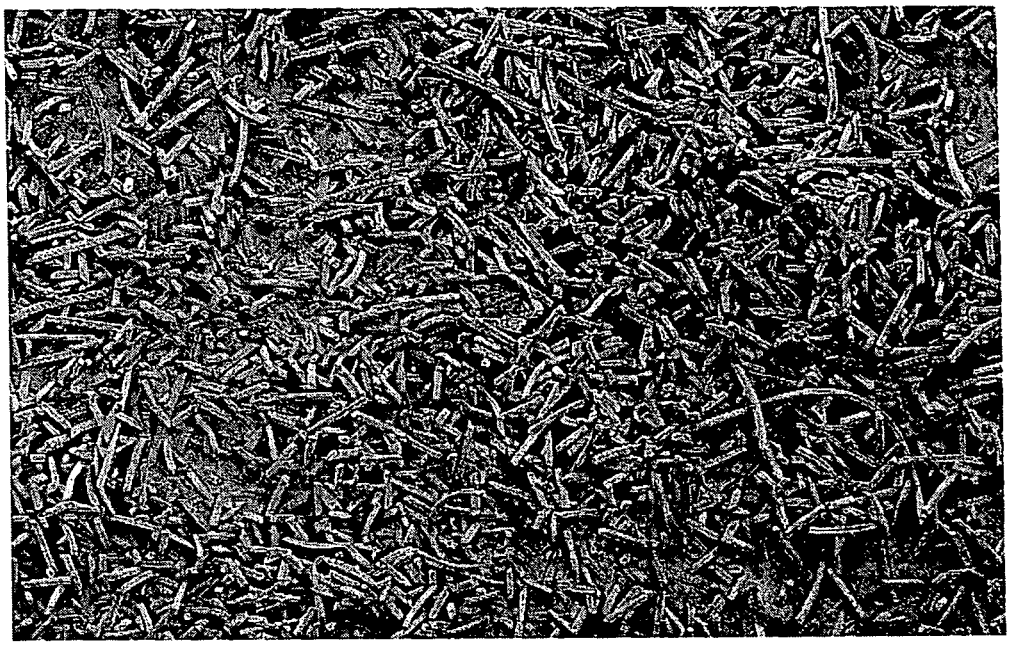
FIG. 13 is a scanning electron microscopy image (×50) of a surface morphology of the micro-fibers described in example 2.

Depending on the conditions to which the homogenous dispersion is subjected, the compositions may be in various forms. For example, the compositions may be in the form of a porous foam, whereby the oxidized cellulose particles are dispersed in a porous foam binder component to form a porous foam sponge, as depicted in FIGS. 1 thru 9b and as described in Examples 1a-1c; or to form porous foam beads as depicted in FIGS. 10a thru 11b and as described in Example 3, depending on the methods used to prepare the composition. In such cases, the particles may be bound within the structure of the porous foam binder component where they may provide hemostatic properties to the composition. At the same time, the porous nature of the polymeric binder component allows greater exposure of the binder to water within the body. The compositions also may take the form of a porous agglomerate of particles and polymer binder, as depicted in FIGS. 12a and 12b and as described in Example 4. In such a case, the porous polymeric binder component may take on a more fibrous structure that is intertwined with the oxidized cellulose particles, as opposed to a foam structure of the sponge or beads. Again, the porous nature of the agglomerates, due in part to the fibrous structure of the binder component, permits greater exposure of the polymer binder to the water in the body. In both cases, the surface area of the binder is maximized so as to provide faster and more extensive hydration by water in the body, which in turn leads to faster and more extensive sealing properties to aid in the hemostatic properties of the oxidized cellulose particles. Such compositions may be further processed into various hemostatic devices.

One method of making the porous foam sponge composition used to make hemostatic devices of the present invention is to dissolve the water-soluble or water-swellable polymer in an appropriate solvent for the polymer to prepare a homogenous polymer solution; contact the oxidized cellulose particles with an appropriate amount of the polymer solution by homogenization, such that the oxidized cellulose particles are dispersed in the polymer solution; and then flash-freeze the polymer solution having the particles and dry/remove the solvent from the frozen structure by, for example, lyophilization at a pressure ranging preferably from 0-250 mtorr, more preferably from 0-200 mtorr, at a temperature ranging from 0° C. to −50° C., for a time duration ranging from 10-14 hours. Lyophilization removes the solvent by sublimation, leaving a porous foam sponge having the oxidized cellulose particles dispersed throughout the porous foam binder component.

During the lyophilization process, several parameters and procedures are important to produce compositions having mechanical properties suitable for use in hemostatic devices. The type of microporous morphology developed during the lyophilization is a function of several factors, such as the solution thermodynamics, freezing rate, temperature to which it is frozen, and concentration of the solution. To maximize the surface area of the porous foam beads of the present invention, the homogenized polymer solution/particles may first be quickly frozen at lower than 0° C., preferably at about −50° C., i.e. by dripping into liquid nitrogen, followed by removal of the solvent at a pressure ranging preferably from 0-250 mtorr, more preferably from 0-200 mtorr, at a temperature ranging from 0° C. to −50° C., for a time duration ranging from 10-14 hours; leaving porous foam beads having the oxidized cellulose particles dispersed throughout the porous foam binder component.

One method of making the porous fibrous agglomerates that may be used to make hemostatic devices of the present invention is to dissolve the water-soluble or water-swellable polymer in an appropriate solvent for the polymer to prepare a homogenous polymer solution; contact the oxidized cellulose particles with an appropriate amount of the polymer solution by homogenization, such that the oxidized cellulose particles are dispersed in the polymer solution; dripping the homogenized dispersion into isopropanol to precipitate the water-soluble or water-swellable polymer and to form fibrous agglomerates having oxidized cellulose dispersed therein, and then flash-freeze and dry/remove the solvent from the fibrous agglomerates by, for example, lyophilization at a pressure ranging preferably from 0-250 mtorr, more preferably from 0-200 mtorr, at a temperature ranging from 0° C. to −50° C., for a time duration ranging from 10-14 hours, leaving porous agglomerates having the oxidized cellulose particles dispersed throughout a fibrous structure of porous polymeric binder component.

If the ratio of the water-soluble or water-swellable polymer to oxidized cellulose particles is too low, the polymer does not provide an effective seal to physically block the bleeding, thus reducing the hemostat properties. If the ratio is too high, the hemostat device will be too stiff or too brittle to conform to wound tissue in surgical applications, thus adversely affecting the mechanical properties necessary for handling by the physician in placement and manipulation of the device. A preferred weight ratio of polymer to oxidized cellulose is from about 1:99 to about 15:85. A more preferred weight ratio of polymer to oxidized cellulose is from about 3:97 to about 10:90.

As discussed above, hemostatic devices utilizing the compositions so produced may be of various forms. When the composition is in the form of a porous foam sponge, its thickness is preferably greater than 2.0 mm. More preferably, the thickness of the sponge ranges from 2.0 to 10 mm. Most preferably, the thickness of the sponge ranges from 2.5 to 5.5 mm, and the average designated nominal particle size of the oxidized cellulose particles is from about 0.80 mm to about 2.2 mm. A hemostatic device utilizing this composition remains very flexible, conforms to a bleeding site and retains good tensile and compressive strength to withstand handling during application. The hemostatic device can be cut into different sizes and shapes to fit the surgical needs, or can be rolled up or packed into irregular anatomic areas or to facilitate use in endoscopic/less invasive procedures.

In addition, non-woven hemostatic devices may be prepared by compacting the porous foam beads or fibrous agglomerates such as may be practiced in producing non-woven felt fabrics. Foam beads or fibrous agglomerates may be made to such a size as to permit the formation of pastes or slurries comprising the beads or agglomerates, whereby the pastes or slurries may be applied to or injected into areas requiring hemostatsis. Such pastes and slurries are reported in the art and once having the benefit of this disclosure those skilled in the art would readily be able to prepare such devices. Other embodiments of hemostatic devices contemplated by the inventions include a hemostatic powder, a hemostatic patch, or a hemostatic plug whereby beads or agglomerates are compressed or formulated with excipients.

As noted above, in certain embodiments of the invention, a hemostatic agent, a biologic or therapeutic compounds, such as drugs or pharmaceutical agents, or combinations thereof, that otherwise may be sensitive to the low pH of conventional carboxyl-oxidized cellulose-containing wound dressings, may be incorporated into hemostatic devices of the present invention utilizing an aldehyde-oxidized cellulose, without having to adjust pH prior to incorporation into the dressing. Moreover, protein-based hemostatic agents, such as thrombin, fibrin or fibrinogen, if bound to the hemostatic device, can enhance the hemostatic property of aldehyde-oxidized cellulose hemostatic device and reduce the risk of thrombosis caused by free hemostatic agents migrating into the blood stream. Hemostatic agents may be bound to the hemostatic device either by chemical of physical means. Agents may be covalently conjugated with aldehyde groups pendant from the polysaccharide in one instance, thus chemically binding the agent to the hemostatic device. Preferably, the hemostatic agents are physically bound to the hemostatic device via incorporation into the polymer and immobilized, i.e. bound, via lyophilization.

Hemostatic devices made from an aldehye-oxidized cellulose may comprise hemostatic agents, including but not limited to thrombin, fibrinogen or fibrin, in an amount effective to provide rapid hemostasis and maintain effective hemostasis in cases of severe bleeding. If the concentration of the hemostatic agent in the wound dressing is too low, the hemostatic agent does not provide an effective proagulant activity to promote rapid clot formation upon contact with blood or blood plasma. A preferred concentration range of thrombin in the hemostatic device is from about 0.001 to about 1 percent by weight. A more preferred concentration of thrombin in the hemostatic device is from about 0.01 to about 0.1 percent by weight. A preferred concentration range of fibrinogen in the hemostatic device is from about 0.1 to about 50 percent by weight. A more preferred concentration of fibrinogen in the hemostatic device is from about 2.5 to about 10 by weight. A preferred concentration range of fibrin in the hemostatic device is from about 0.1 to about 50 percent by weight. A more preferred concentration of fibrin in the hemostatic device is from about 2.5 to about 10 by weight.

In certain embodiments, the aldehyde-oxidized cellulose may comprise covalently conjugated therewith a hemostatic agent bearing an aldehyde-reactive moiety. In such embodiments, the aldehyde moiety of aldehyde-oxidized regenerated cellulose can readily react with the amine groups present on the amino acid side chains or N-terminal residues of thrombin, fibrinogen or fibrin, resulting in forming a conjugate of the hemostatic agent with the aldehyde-oxidized regenerated cellulose covalently linked by a reversible imine bond. The imine bonded aldehyde-oxidized regenerated cellulose/hemostatic agent conjugate may then be further reacted with a reducing agent such as sodium borohydride or sodium cyanoborohydride to form an irreversible secondary amine linkage. In such embodiments of the invention, the hemostatic agent is dispersed at least on the surface of the hemostatic device, and preferably at least partially through the hemostatic device, bound reversibly or irreversibly to the aldehyde-oxidized cellulose.

In preferred embodiments of the present invention, the hemostatic agent, such as thrombin, fibrinogen, or fibrin is constituted in an aqueous solution of a non-acidic, water-soluble or water-swellable polymer, as described herein above, including but not limited to methyl cellulose, hydroxyalkyl cellulose, water-soluble chitosan, salts of carboxymethyl carboxyethyl cellulose, chitin, salts of hyaluronic acid, alginate, propylene glycol alginate, glycogen, dextran, carrageenans, chitosan, starch, amylose, poly-N-glucosamine, and the aldehyde-oxidized derivatives thereof. A homogenized suspension of aldehyde-oxidized cellulose and an aqueous solution of hemostatic agent and the water-soluble or water-swellable polymer, can be rapidly lyophilized using known methods that retain therapeutic activity. When constructed thusly, the hemostatic agent will be substantially homogenously dispersed through the polymeric substrate formed during lyophilization.

One skilled in the art, once having the benefit of this disclosure, will be able to select the appropriate hemostatic agent, water-soluble or water-swellable polymer and solvent therefore, and levels of use of both the polymer and hemostatic agent, depending on the particular circumstances and properties required of the particular hemostatic device.

Hemostatic devices of the present invention are best exemplified in the figures prepared by scanning electron microscope. The samples were prepared by cutting 1-cm$^2$ sections of the dressings by using a razor. Micrographs of both the first surface and opposing second surface, and cross-sections were prepared and mounted on carbon stubs using carbon paint. The samples were gold-sputtered and examined by scanning electron microscopy (SEM) under high vacuum at 4 KV.

While the following examples demonstrate certain embodiments of the invention, they are not to be interpreted as limiting the scope of the invention, but rather as contributing to a complete description of the invention.

EXAMPLE 1a

Chopped CORC Fabric/Na—CMC Porous Patch (10/40) Preparation

One gram of sodium salt of CMC (Na—CMC, from Aqualon® 7M8SF) was dissolved in 99 grams of deionized water. After complete dissolution of the polymer, 15 grams of the Na—CMC solution was transferred into a crystallization dish with a diameter of 10 cm. A piece of Surgicel Nu-Knit® fabric with a diameter of 9.8 cm (about 1.3 gram) was chopped with a Thomas-Wiley® Laboratory Mill, Intermediate Model cutting blade then passed through a USA standard Testing Sieve (mesh size=10, A.S.T.M.E.-11 Specification) to yield fibers with an average designated nominal particle size of 1.7 mm. The chopped fabric was placed in the CMC—Na solution in the crystallization dish. The suspension of the chopped fabric in CMC—Na solution was placed in an Ultra-TURRAX® T18 DIXI midi Dispersers/Homogenizers homogenizer and homogenized for less than 5 min until the loose chopped fabric is evenly distributed in the solution. The homogeneous solution was then lyophilized in the dish overnight. A very flexible patch was formed (basis weight=40, thickness=5 mm). The patch was further dried at room temperature under vacuum.

EXAMPLE 1b

Chopped CORC Fabric/Na—CMC Porous Patch (20/40) Preparation

One gram of sodium salt of CMC (Na—CMC, from Aqualon® 7M8SF) was dissolved in 99 grams of deionized water. After complete dissolution of the polymer, 15 grams of the Na—CMC solution was transferred into a crystallization dish with a diameter of 10 cm. A piece of Surgicel Nu-Knit® fabric with a diameter of 9.8 cm (about 1.3 gram) was chopped with an Thomas-Wiley® Laboratory Mill, Intermediate Model cutting blade then passed through a USA standard Testing Sieve (mesh size=20, A.S.T.M.E.-11 Specification) to yield fibers with an average designated nominal particle size of 0.85 mm. The chopped fabric was placed in the CMC—Na solution in the crystallization dish. The suspension of the chopped fabric in CMC—Na solution was placed in an Ultra-TURRAX® T18 DIXI midi Dispersers/Homogenizers homogenizer and homogenized for less than 5 min until the loose chopped fabric is evenly distributed in the solution. The homogeneous solution was then lyophilized in the dish overnight. A very flexible patch was formed (basis weight=40, thickness=5 mm). The patch was further dried at room temperature under vacuum.

EXAMPLE 1c

Chopped CORC Fabric/Na—CMC Porous Patch (40/40) Preparation

One gram of sodium salt of CMC (Na—CMC, from Aqualon® 7M8SF) was dissolved in 99 grams of deionized water. After complete dissolution of the polymer, 15 grams of the Na—CMC solution was transferred into a crystallization dish with a diameter of 10 cm. A piece of Surgicel Nu-Knit® fabric with a diameter of 9.8 cm (about 1.3 gram) was chopped with an Thomas-Wiley® Laboratory Mill, Intermediate Model cutting blade then passed through a USA standard Testing Sieve (mesh size=40, A.S.T.M.E.-11 Specification) to yield fibers with an average designated nominal particle size of 0.43 mm. The chopped fabric was placed in the CMC solution in the crystallization dish. The suspension of the chopped fabric in CMC—Na solution was placed in an Ultra-TURRAX® T18 DIXI midi Dispersers/Homogenizers homogenizer and homogenized for less than 5 min until the loose chopped fabric is evenly distributed in the solution. The homogeneous solution was then lyophilized in the dish overnight. A very flexible patch was formed (basis weight=40, thickness=5 mm). The patch was further dried at room temperature under vacuum.

EXAMPLE 2

CORC Micro-fibers/Na—CMC Patch Preparation

CORC Fibrillar was first immersed in liquid nitrogen in a stainless steel foil pouch then the $LN_2$ containing pouch filled with CORC Fibrillar will go through a dual wheel/roller at 6 in/min, yielding CORC powders, micro fibers or fine particles of various length/sizes. Particles of desired sizes can be subsequently separated with USA standard Testing Sieves (A.S.T.M.E.-11 Specification) of different mesh sizes (20-400), yielding micro-fibers of length ranging from 0.035-0.86 mm. CORC particles/powders/micro fibers thus prepared were placed in the CMC—Na solution in the crystallization dish. The suspension of the CORC particles/powders/micro fibers in CMC—Na solution was placed in an Ultra-TURRAX® T18 DIXI midi Dispersers/Homogenizers homogenizer and homogenized until the loose CORC particles/powders/micro fibers are evenly distributed in the CMC—Na (Aqualon® 7M8SF) solution. The homogeneous solution was then lyophilized in the dish overnight. A very flexible patch was formed (basis weight=40, thickness=5 mm). The patch was further dried at room temperature under vacuum.

EXAMPLE 3

CORC/Na—CMC Micro-porous Beads Preparation

CORC Fibrillar is first emerged in liquid nitrogen in a stainless steel foil pouch then the $LN_2$ containing pouch filled with CORC Fibrillar will go through a dual wheel/roller at 6 in/min, yielding CORC powders, micro fibers or fine particles of various length/sizes. Particles of desired sizes can be subsequently separated with sieves. CORC particles/powders/ micro fibers thus prepared were placed in the CMC—Na Aqualon® 7M8SF solution in the crystallization dish. The suspension of the CORC particles/powders/micro fibers in CMC—Na solution was placed in an Ultra-TURRAX® T18 DIXI midi Dispersers/Homogenizers homogenizer and homogenized until the loose CORC particles/powders/micro fibers are evenly distributed in the CMC—Na solution. The homogeneous solution in the dish was transferred via a tube into $LN_2$ bath. The CORC/CMC—Na suspension was instantly freezed yielding micro-porous beads of various diameters, ranging from 0.2-9 mm, and lyophilized overnight. The micro porous-beads were further dried at room temperature under vacuum.

EXAMPLE 4

Fibrous CORC/Na—CMC Agglomerates Preparation

CORC Fibrillar is first emerged in liquid nitrogen in a stainless steel foil pouch then the $LN_2$ containing pouch filled with CORC Fibrillar will go through a dual wheel/roller at 6 in/min, yielding CORC powders, micro fibers or fine particles of various length/sizes. Particles of desired sizes can be subsequently separated with sieves. CORC particles/powders/micro fibers thus prepared were placed in the CMC—Na (Aqualon® 7M8SF) solution in the crystallization dish. The suspension of the CORC particles/powders/micro fibers in CMC—Na solution was placed in homogenizer and homogenized until the loose CORC particles/powders/micro fibers are evenly distributed in the CMC—Na solution. The homogeneous solution in the dish was transferred via a tube into Isopropanol (IPA) bath to facilitate the precipitation of CORC/CMC—Na composite. Excess amount of (80-95%) of IPA was removed from the precipitated CORC/CMC—Na composite, then the CORC/CMC—Na composite was instantly freezed yielding fibrous agglomerates of various form and lyophilized overnight. The fibrous agglomerates were further dried at room temperature under vacuum.

EXAMPLE 5

Hemostatic Performance of Different Materials in Porcine Splenic Incision Model

A porcine spleen incision model was used for hemostasis evaluation of different materials. The materials were cut into 2.5 cm×1.5 cm rectangles or used as prepared by methods described in the examples above. A linear incision of 1.5 cm with a depth of 0.3 cm was made with a surgical blade on a porcine spleen. After application of the test article, digital tamponade was applied to the incision for 2 minutes. The hemostasis was then evaluated. Additional applications of digital tamponade for 30 seconds each time were used until complete hemostasis was achieved. Fabrics failing to provide hemostasis within 12 minutes were considered to be failures. Table 1 lists the results of the evaluation.

TABLE 1

Hemostatic performance of different materials

| Material | Percent of test samples to achieve hemostasis within the time period | | | | | Maintenance of Hemostasis |
| --- | --- | --- | --- | --- | --- | --- |
| | 0-2 (min) | 2-3 (min) | 3-4 (min) | 4-5 (min) | <12 (min) | |
| Surgical Nu-Knit ® absorbable hemostat | 0% | 0% | 100% | | | Re-bleeding occurred after 4 min |
| Example 1a patch | 100% | | | | | No Re-bleeding occurred |
| Example 1b patch | 100% | | | | | No Re-bleeding occurred |
| Example 1c patch | 100% | | | | | Re-bleeding occurred |
| Example 2 patch | 100% | | | | | No Re-bleeding occurred |
| Example 3 CORC/Na—CMC Micro porous-beads | | 80% | 100% | | | No Re-bleeding occurred |
| Example 4 Fibrous agglomerates | 100% | | | | | No Re-bleeding occurred |
| Surgical gauze | | | | | 0% | Re-bleeding occurred immediately after |

We claim:
1. A process for making a composition useful in a hemostatic device, comprising:
   providing a polymer solution having a water-soluble or water-swellable polysaccharide polymer dissolved in a suitable solvent therefore wherein said polymer is sodium carboxymethyl cellulose,
   providing biocompatible, oxidized cellulose particles that comprise carboxylic-oxidized regenerated cellulose and having an average designated nominal size from about of 0.035 to about 4.35 mm,
   contacting said polymer solution with said oxidized cellulose particles under conditions effective to disperse said oxidized cellulose particles homogenously throughout said polymer solution to form a homogenous dispersion,
   subjecting said polymer solution having said particles dispersed throughout to conditions effective to solidify said homogenous dispersion; and
   removing said solvent from the solidified dispersion by lyophilization, thereby forming said composition in the form of a porous sponge having a thickness of between 2 mm and 10 mm comprising said particles and a porous, water-soluble or water-swellable polysaccharide polymer binder component.
2. The process of claim 1 wherein the weight ratio of said sodium carboxymethyl cellulose to said oxidized cellulose particles is from about 1:99 to about 20:80.
3. The process of claim 1 wherein the weight ratio of said sodium carboxymethyl cellulose to said oxidized cellulose particles is from about 3:97 to about 10:90.

* * * * *